June 29, 1954 J. M. GARABEDIAN Plant Pat. 1,287

NECTARINE TREE

Filed Jan. 19, 1953

WITNESSES

Addison E. Avery

Vernon Carson

INVENTOR

JOHN M. GARABEDIAN

Webster & Webster

ATTYS.

Patented June 29, 1954 Plant Pat. 1,287

UNITED STATES PATENT OFFICE 1,287

NECTARINE TREE

John M. Garabedian, Fresno, Calif.

Application January 19, 1953, Serial No. 332,135

1 Claim. (Cl. 47—62)

The present invention relates to a new and distinct variety of nectarine tree which bears relatively late ripening fruit; the variety having general resemblance to the Tioga variety of nectarine, but distinguishable thereover by fruit which is clingstone, and which has a ripening period approximately four weeks later; ripening at a harvest time when no other comparable variety is available.

Additionally, the instant variety of nectarine tree is characterized, as compared to the Tioga variety, by fruit which—while having substantially the same color—is considerably larger and better eating, not being tart and pithy, as is the Tioga.

The present variety of nectarine tree was originated by me upon my ranch near Madera, county of Madera, State of California, in the following manner:

Seeds from the Tioga (unpatented) and Jordana (United States Plant Patent No. 1141) varieties of nectarines; together with seeds from the Rio Oso Gem (United States Plant Patent No. 84), Royal Fay Elberta (United States Plant Patent No. 795), and Kirkman Gem (United States Plant Patent No. 506) varieties of peaches were gathered; there having been one each of the trees of the above varieties growing side by side, and the seeds having resulted from open-pollination. The seeds so collected were planted, and from such planting approximately 150 seedlings resulted. These seedlings were permitted to open-pollinate, and among such seedlings, while under careful observation by me, the instant variety—which was one of the Tioga seedlings—was found to be characterized by novel features, as above enumerated.

Since its discovery I have successfully asexually reproduced the present variety of nectarine by budding the same onto mature peach trees at my ranch located as aforesaid; the reproductions having been found to carry forward each and every one of the novel characteristics of the parent tree.

Figures 1, 2:
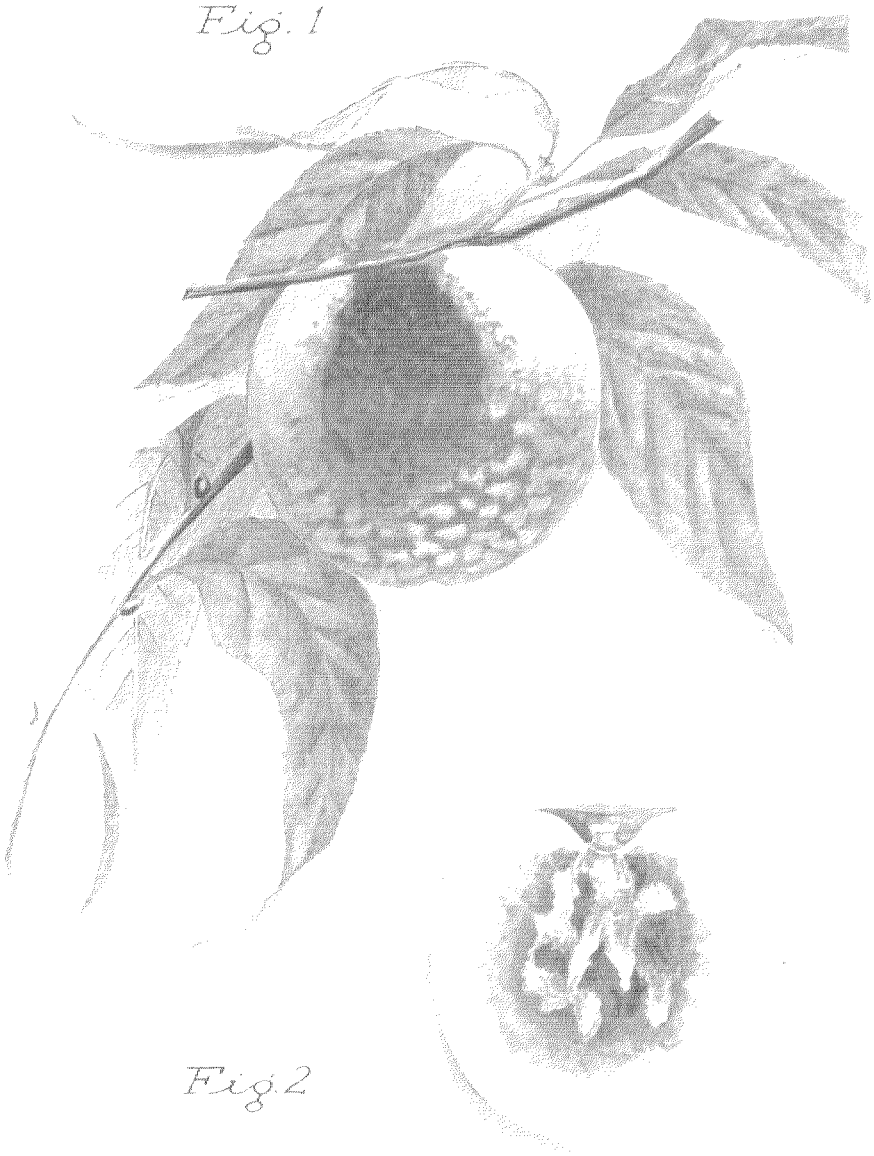
Fig. 1 is an elevation of one of the fruit, together with stems and leaves.
Fig. 2 is a sectional view of one of the fruit, with the stone exposed.

Referring now more specifically to the pomological details of this new and distinct variety of nectarine tree, the following is an outline description thereof; all major color plate identifications being by reference to Maerz and Paul Dictionary of Color:

Tree: Medium size; medium vigorous; upright—spreading; dense to open; vase formed; productive; regular bearer.

Trunk: Medium size; medium smooth.

Branches: Medium size; medium smooth. Color—greyish brown (7-E-8). Shoots—yellowish green, glossy.

*Lenticels*: Medium number. Large to medium size.

Leaves: Medium size. Average length—6½" to 7"; average width—1⅜" to 2". Acuminate—lanceolate; acutely pointed; medium thickness; smooth. Color: top side—medium green (23-L-3); under side—lighter green (22-K-3).

*Margin.*—Glandular—crenate.

*Petiole.*—Medium to short length; medium thickness.

*Glands.*—Average—five (four to seven). Opposite; large size; reniform. Color—green. Position—one to four on petiole just below the blade; two to four on blade at or near base.

Flower buds: Medium length; ovate; plump; free; pubescent.

Flowers: Average date of first bloom—March 4th. Average date of full bloom—March 10th. Size—medium. Color—pink.

Fruit: First picking—September 7, 1952. Last picking—September 14, 1952.

*Maturity* when described.—Eating (September 10, 1952).

*Size.*—Large; uniform. Average diameter axially—2¼" to 2½"; average transversely in suture plane—2⅝" to 2⅞".

*Form.*—Uniform; symmetrical; globose; only slightly compressed laterally.

*Suture.*—A shallow broad groove extending from base to beyond but discontinuous at apex, with marked depression just ventral to pistil point.

*Ventral surface.*—Rounded; lipped toward apex throughout both sides; lips equal.

*Cavity.*—Flaring; rounded. Slightly elongated in suture plane, with suture showing on one side. Average depth—⅝" to ¾"; average breadth—1⅛" to 1¼".

*Base.*—Rounded to truncate.

*Apex.*—Rounded in cheek aspect; depressed along suture; apical.

*Skin.*—Thick; medium; tenaceous to flesh. Tendency to crack—none. Color—yellow (10-L-5 shading to 11-L-7), deeply blushed on sunny side with red (5-L-9), shading darker (6-L-6) toward the cavity, with relatively large yellow spotting (10–L–6) on the lower portion of the fruit.

Flesh:

*Color.*—Yellow (10–L–6), mottled very red (4–L–5) next to stone.

*Amygdalin.*—Moderate to scant.

*Juice.*—Moderate; rich.

*Texture.*—Firm; medium; crisp; meaty.

*Fibers.*—Abundant; tender.

*Ripens.*—Evenly.

*Flavor.*—Mild.

*Aroma.*—Distinct.

*Eating quality.*—Good.

Stone: Cling. Adheres to flesh over entire surface.

*Size.*—Medium. Average length—1¼'' to $1\frac{5}{16}$''; average breadth—1⅛'' to $1\frac{3}{16}$''; average thickness—⅞'' to 1''.

*Form.*—Broad oval.

*Base.*—Straight.

*Hilum.*—Oval.

*Apex.*—Rounded.

*Sides.*—Unequal, dorsal edge bulged apically.

*Surface.*—Pitted throughout.

*Ridges.*—Rounded.

*Pits.*—Circular—elongated.

*Ventral edge.*—Thick, without wing.

*Dorsal edge.*—Full, with deep broad groove throughout.

*Ridges.*—Continuous.

*Color.*—Strongly deep purple-red (55–L–12).

*Tendency to split.*—Slight.

*Use.*—Market; eating, dessert.

*Keeping quality.*—Good.

*Shipping quality.*—Good.

The tree and its fruit herein described may vary in slight detail due to climatic and soil conditions under which the variety may be grown.

Having thus described my invention, I claim:

A new and distinct variety of nectarine tree, substantially as described and illustrated, bearing clingstone fruit which, as compared to the Tioga variety of nectarine, is characterized by fruit of similar color but larger size, ripening approximately four weeks later than said Tioga; the flesh of the fruit of the instant variety being mild in flavor, medium texture, crisp, and meaty as compared to the tart, pithy flesh of the Tioga.

No references cited.